United States Patent [19]

Sato et al.

[11] Patent Number: 4,468,459

[45] Date of Patent: Aug. 28, 1984

[54] PROCESS FOR THE PREPARATION OF POLYPRENYL KETONE DERIVATIVES

[75] Inventors: Akio Sato, Yatabemachi; Kenji Nakajima, Sakuramura; Yoshimasa Takahara, Narashino; Shizumasa Kijima, Niiza; Isao Yamatsu, Kawaguchi; Kouichi Suzuki, Kakamigahara; Takeshi Suzuki, Abiko; Toshihiko Nakamura, Tokyo, all of Japan

[73] Assignees: Eisai Co., Ltd.; Director General of the Agency of Industrial Science and Technology, both of Tokyo, Japan

[21] Appl. No.: 446,817

[22] Filed: Dec. 3, 1982

Related U.S. Application Data

[62] Division of Ser. No. 312,068, Oct. 16, 1981.

[30] Foreign Application Priority Data

Oct. 23, 1980 [JP] Japan ................................ 55-148831

[51] Int. Cl.$^3$ ........................... C12P 7/40; C12P 7/26
[52] U.S. Cl. ..................................... 435/136; 435/148
[58] Field of Search ................................. 435/148, 136

[56] References Cited

U.S. PATENT DOCUMENTS 3,748,231  7/1973  Hosler et al. ....................... 435/148

Primary Examiner—Alvin E. Tanenholtz
Attorney, Agent, or Firm—Flynn, Thiel, Boutell & Tanis

[57] ABSTRACT

Longer carbon chain polyprenyl ketone derivatives are prepared by cultivating Nocardia strain FERM-P No. 1609 in the presence of shorter carbon chain polyprenyl ketones.

2 Claims, No Drawings

PROCESS FOR THE PREPARATION OF POLYPRENYL KETONE DERIVATIVES

This is a division of application Ser. No. 312,068, filed Oct. 16, 1981.

This invention relates to novel polyprenyl ketone derivatives having the general formula:

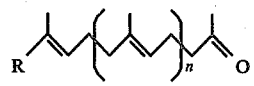
(I)

in which n is an integer of 1-5, and R represents a hydroxymethyl, formyl or carboxyl group, and a process for the preparation of the same.

Polyprenyl-type compounds such as polyprenyl alcohols and their esters, polyprenyl carboxylic acids and their esters, and polyprenyl ketones are known to have the antiulcer activity and the hypotensive activity, as disclosed in Japanese Patent Provisional Publications No. 52-144614, No. 53-145922, No. 54-5043, No. 54-67037, and No. 54-76513. Further, polyprenyl alcohols are known to be employable as starting materials for the preparations of pharmaceutically active compounds such as Coenzyme $Q_{10}$.

The compound of the present invention is of value as an intermediate compound for preparing the above-mentioned polyprenyl-type compounds, and also is of value per se as an anti-ulcer agent.

The compound of the invention can be converted to the polyprenyl-type compounds, for instance, via a sulfone derivative as disclosed in Japanese Patent Provisional Publications No. 53-103444 and No. 53-103445. The compound of the invention can be employed as an intermediate compound for the synthesis process, in the original form where R is the hydroxymethyl group, or in the form of the hydroxymethyl group upon reduction where R is the formyl or carboxyl group.

The reactions can be illustrated, for instance, by the following reaction equations.

(1) Polyprenyl ketone

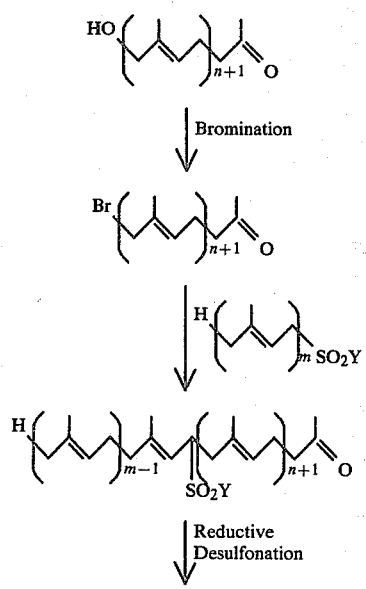

-continued

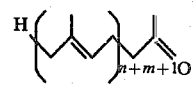

In the above reaction equations, n has the same meaning as above, m is an integer, and Y represents an aryl or alkyl group.

(2) Polyprenyl carboxylic acid and its derivative

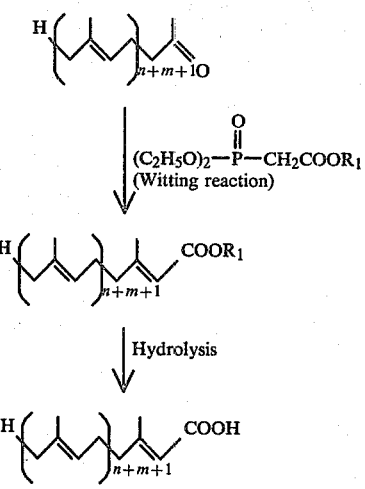

In the above reaction equations, n amd m have the same meanings as above, and $R_1$ represents a lower alkyl group.

(3) Polyprenyl alcohol

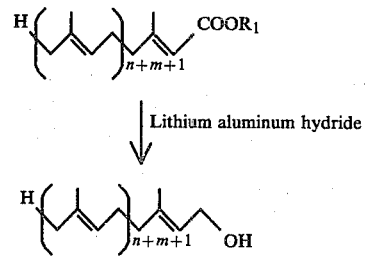

In the above reaction equations, n, m and $R_1$ have the same meanings as above.

As shown in the above (1)-(3) sections, the employment of the compound of the invention in the preparation of polyprenyl-type compounds can prolong the carbon chain to an optionally selected level in terms of the carbon number.

As stated hereinbefore, various compounds having a functional group at the terminal of their isoprenoid chain are known. However, the selective introduction of a functional group into another terminal of the above compound is difficult from the view point of the chemical synthesis process. This difficulty increases where the isoprenyl chain is relatively long. Accordingly, the present invention provides a process for the preparation of the subject compound involving microbiological oxidation. More in detail, the compound of the invention can be obtained by microbiological oxidation of polyprenyl ketone by the use of a microorganism belonging to the genus Nocardia.

The genus Nocardia named BPM 1613 was deposited with the Fermentation Research Institute, the Agency of Industrial Science and Technology, located at 1-1-3, Higashi, Tsukuba-Yatabe-machi, Ibaraki-prefecture, Japan on Sept. 18, 1972 and has been added to its permanent collection of microorganisms as FERM-P No. 1609. The same genus Nocardia as above was deposited also with the Institute for Fermentation, Osaka, located at 2-17-15, Juso-Honmachi, Yodogawa-ku, Osaka, Japan on Jan. 9, 1981 and has been added to its permanent collection of microorganisms as IFO 14101. This strain can be employed in the invention and has particulars as given below. The color is expressed according to the "Color Standard" published by Nippon Shikisai Kenkyusho (Japan Color Research Center), Japan.

A. Form of Cells

The present strain shows characteristic orange to pink color in almost all culture media, as seen from the cultural characteristics given below. A young vegetative cell grows in a mycelial form, and the branching is rarely observed. In an aged cultivated system, the hypha is divided to form a bacillus (0.4—0.6×1.8—2.4 μ). Gram positive. No flagellum. Negative on the acid-fast stain according to the Ziehl-Nielsen method. Aerial mycelium is not observed.

B. Cultural Characteristics on Various Media
(1) Sucross - Nitrate Agar Medium (30° C.): poor growth; pink colored colony; no diffusive pigment
(2) Glucose - Asparagine Agar Medium (30° C.): no growth
(3) Glycerol - Asparagine Agar Medium (30° C.): poor growth; pink colored colony; no diffusive pigment
(4) Starch Agar Medium (30° C.): no growth
(5) Tyrosine Agar Medium (30° C.): poor growth; grayish white colored colony; no diffusive pigment
(6) Nutrient Agar Medium (30° C.): moderate growth; orange colored colony; no diffusive pigment
(7) Yeast - Malt Agar Medium (30° C.): rich growth; orange colored colony; no diffusive pigment
(8) Oatmeal Agar Medium (30° C.): moderate growth; orange colored colony; no diffusive pigment
(9) Calcium Maleate Agar Medium (27° C.): moderate growth; pink colored colony
(10) Egg-albumin Medium (slant, 27° C.): poor growth; white colony
(11) Potato Section Medium (27° C.): moderate growth; pale orange colored colony
(12) Carrot Section Medium (27° C.): moderate growth; pale pink colored colony C. Physiological characteristics
(1) Growth Temperature Range (on Nutrient Agar Medium, slant): 20°-42° C.
(2) Liquefaction of Gelatin: megative
(3) Hydrolysis of Starch: negative
(4) Coagulation of Defatted Milk, Peptonization: negative
(5) Litmus Milk: no change
(6) Production of Melanine-like Pigment: negative
(7) Reduction of Nitrate: positive
(8) No gas or acid production from L-arabinose, D-xylose, D-glucose, D-fructose, sucrose, D-mannitol, glycerol, lactose, D-galactose, D-mannose, maltose, trehalose and starch
(9) Catalase Test: negative
(10) Production of Indole: negative
(11) Production of Hydrogen Sulfide: negative C. Assimilability for Various Carbon Sources
(Pridham-Gottlieb Agar Medium, 30° C., 7 days)
L-arabinose (+), D-xylose (+), D-glucose (++), D-fructose (++), sucrose (++), inositol (+), L-rhamnose (−), raffinose (+), D-mannitol (+) (In the above, (++) means moderate growth, (+) means poor growth, and (−) means no growth)

The above-identified strain, having been cultivated on the Glycerol-Kelner-Morton Medium in accordance with the method described by Arai, et al., in Journal of General Applied Microbiology, 9, 119 (1963): The Actinomycetales, The Jena International Symposium on Taxonomy, 273 (1968), gives absorption bands characteristic of the genus Nocardia on the IR spectrum, that is, I: C & E types, II: C type, III: C type, and IV: D type.

Upon studying the above-described characteristics of the strain with reference to Bergey's Manual of Determinative Bacteriology, Seventh edition, and Waksman's The Actinomycetes, Volume 2, it has been decided that the strain belongs to the genus Nocardia.

A process for the preparation of the compound of the invention is described below.

The compound of the invention having the general formula:

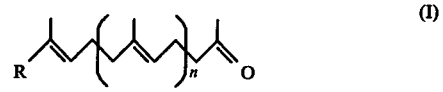
(I)

in which n is an integer of 1-5, and R represents a hydroxymethyl, formyl or carboxyl group can be obtained by cultivating a microorganism belonging to the genus Nocardia and showing the oxidizing activity on a compound having the general formula:

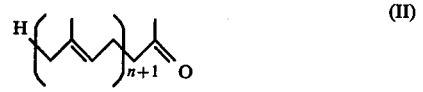
(II)

in which n has the same meaning as above in a culture medium containing a compound of the general formula (II), and recovering the oxidized product from the cultured medium.

The cultivation procedure is described more concretely hereinbelow.

The components of the culture medium can be optionally chosen from those employed conventionally, except for the necessary inclusion of the compound of the general formula (II) as the carbon source. Examples of the nitrogen sources include nitrates such as potassium nitrate, sodium nitrate and ammonium nitrate; ammonium salts such as ammonium chloride, ammonium sulfate and ammonium phosphate; ammonia; and urea. If necessary, inorganic salts such as potassium phosphate, sodium phosphate, magnesium sulfate, ferrous sulfate and manganese sulfate; and organic nutrient sources such as vitamins and amino acids; and yeast extract, corn steep liquor and malt extract which contain the vitamins and amino acids can be incorporated, as well.

The medium is preferably adjusted to have the pH value in the range of 6-8. The cultivation is generally carried out under aerobic conditions such as under aeration and agitation at 20°-40° C. for 2-5 days.

After the cultivation is complete, the cultivation product is extracted with an organic solvent to recover the compound of the invention. Examples of the solvents for extraction include ethyl ether, benzene and chloroform. The product can be subjected to the silica gel column chromatography to separate and purify the compound of the invention.

The unreacted starting material can be recovered by the above-described extracting procedure and column chromatography, and then can be circulated as the starting material for the following run.

The microbiological oxidation of the process of the invention gives a mixture of different products having hydroxymethyl, formyl and carboxyl groups, independently, as the terminal group (R of the general formula (I)), depending upon the extent of the oxidation. The constitution of the product, accordingly, can be varied depending upon the kind of the culture medium, the cultivation period, and so forth.

The present invention is further described more in detail by the following examples.

EXAMPLE 1

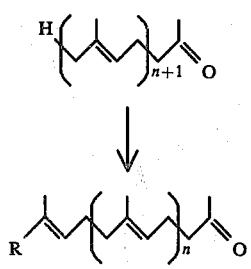

The strain (BPM 1613, FERM-P No. 1609) belonging to the genus Nocardia was precultivated under shaking at 30° C. for 4 days in 50 ml of a medium comprising 2% of n-paraffin, 0.5% of $NaNO_3$, 0.15% of $KH_2PO_4$, 0.15% of $Na_2HPO_4$, 0.05% of $MgSO_4.7H_2O$, 0.001% of $FeSO_4.7H_2O$, 0.001% of $CaCl_2.2H_2O$, and 0.02% of yeast extract and having the pH value of 7.2

Then, the so obtained precultural broth was inoculated, in the volume ratio of 8%, into a jar fermenter (for fermentation of 1 liter medium): a medium having the same composition as defined above except for substituting the n-paraffin (2%) by the compound of the general formula (II) (1%). The cultivation was carried out under aerationagitation conditions at 30° C. for 3 days. After the cultivation was complete, the cultivation product was extracted with ethyl ether. The thin layer chromatograpny of the extract indicated productions of the compounds having hydroxymethyl, formyl and carboxyl groups, respectively, as the terminal R group.

The solvent was then removed from the ethyl ether extract by evaporation, and the residue was purified by the silica gel column chromatography to isolate the main products. In this procedure, hexane and ethyl ether were employed as the eluting solvents.

The results obtained in the above process are set forth in Table 1. It was found that by-products were hardly produced and almost all the starting material that had been actually reacted was converted to the desired product. Almost all unconverted starting material could be recovered with the silica gel column chromatography as mentioned above.

In the example, the following compounds were produced.

10-keto-2,6-dimethyl undeca-2,6-dien-1-carboxylic acid 14-keto-2,6,10-trimethyl pentadeca-2,6,10-trien-1-carboxylic acid 18-keto-2,6,10,14-tetramethyl nonadeca-2,6,10,14-tetraen-1-carboxylic acid 22-keto-2,6,10,14,18-pentamethyl tricosa-2,6,10,14,18-pentaen-1-carboxylic acid 26-keto-2,6,10,14,18,22-hexamethyl heptacosa-2,6,10,14,18,22-hexaen-1-carboxylic acid 10-keto-2,6-dimethyl-undeca-2,6-dien-1-ol 14-keto-2,6,10-trimethyl-pentadeca-2,6,10-trien-1-ol 18-keto-2,6,10,14-tetramethyl nonadeca-2,6,10,14-tetraen-1- ol 22-keto-2,6,10,14,18-pentamethyl tricosa-2,6,10,14,18-pentaen-1-ol 26-keto-:2,6,10,14,18,22-hexamethyl heptacosa-2,6,10,14,18,22-hexaen-1-ol 18-keto-2,6,10,14-tetramethyl nonadeca-2,6,10,14-tetraen-1-al 22-keto-2,6,10,14,18-pentamethyl tricosa-2,6,10,14,18-pentaen-1-al

TABLE 1

(I)

| Product (I) n | R | State Yield (%) | Mass Spectrum (M+) | NMR Spectrum (δ, CDCl₃) |
|---|---|---|---|---|
| 1 | HOOC— | Oil 10.1 | 224 | 1.69 (3H, s), 1.84 (3H, s), 1.93~2.55 (8H, br), 2.10 (3H, s), 5.05 (1H, t, J = 6Hz), 6.87 (1H, t, J = 7Hz), 11.5 (1H, br) |
| 1 | HOH₂C— | Oil 2.8 | 210 | 1.62 (3H, s), 1.66 (3H, s), 1.95~2.50 (9H, br), 2.09 (3H, s), 3.94 (2H, s), 5.04 (1H, t, J = 6Hz), 5.30 (1H, t, J = 7Hz) |
| 2 | HOOC— | Oil 12.6 | 292 | 1.60 (6H, s), 183 (3H, s), 1.95~2.50 (12H, br), 2.10 (3H, s), 4.95~5.15 (2H, br), 6.88 (1H, t, J = 6Hz), 11.0~12.0 (1H, br) |
| 2 | HOH₂C— | Oil 3.2 | 278 | 1.60 (6H, s), 1.65 (3H, s), 1.95~2.50 (13H, br), 2.10 (3H, s), 3.95 (2H, s), 4.95~5.15 (2H, br), 5.30 (1H, t, J = 6Hz) |
| 3 | HOOC— | Oil 16.2 | 360 | 1.60 (9H, s), 1.83 (3H, s), 1.95~2.50 (16H, br), 2.10 (3H, s), 5.00~5.20 (3H, br), 6.87 (1H, t, J = 7Hz), 9.50~10.0 (1H, br) |
| 3 | HOH₂C— | Oil 32.1 | 346 | 1.60 (9H, s), 1.65 (3H, s), 1.95~2.50 (17H, br), 2.09 (3H, s), 3.95 (2H, s), 5.00~5.20 (3H, br), 5.30 (1H, t, J = 6Hz) |
| 3 | OHC— | Oil 1.1 | 344 | 1.60 (9H, s), 1.75 (3H, s), 1.95~2.50 (16H, br), 2.10 (3H, s), 5.10 (3H, br), 6.46 (1H, t, J = 6Hz), 9.50 (1H, s) |
| 4 | HOOC— | Wax 19.7 | 428 | 1.60 (12H, s), 1.81 (3H, s), 1.95~2.50 (20H, br), 2.10 (3H, s), 4.90~5.15 (4H, br), 6.90 (1H, t, J = 7Hz), 11.5~12.0 (1H, br) |

TABLE 1-continued

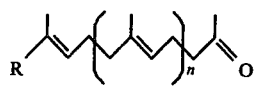

| Product (I) | | State Yield | Mass Spectrum | |
|---|---|---|---|---|
| n | R | (%) | (M+) | NMR Spectrum (δ, CDCl$_3$) |
| 4 | HOH$_2$C— | Wax 14.6 | 414 | 1.60 (12H, s), 1.65 (3H, s), 1.95~2.50 (21H, br), 2.10 (3H, s), 3.95 (2H, s), 4.90~5.15 (4H, br), 5.30 (1H, t, J = 7Hz) |
| 4 | OHC— | Wax 1.6 | 412 | 1.60 (12H, s), 1.76 (3H, s), 1.95~2.50 (20H, br), 2.10 (3H, s), 5.10 (4H, br), 6.47 (1H, t, J = 6Hz), 9.48 (1H, s) |
| 5 | HOOC— | Wax 20.2 | 496 | 1.60 (15H, s), 1.81 (3H, s), 1.95~2.50 (24H, br), 2.08 (3H, s), 4.90~5.15 (5H, br), 6.90 (1H, t, J = 6Hz), 11.0~12.0 (1H, br) |
| 5 | HOH$_2$C— | Wax 18.3 | 482 | 1.60 (15H, s), 1.65 (15H, s), 1.95~2.50 (25H, br), 2.09 (3H, s), 3.95 (2H, s), 4.90~5.15 (5H, br), 5.30 (1H, t, J = 6Hz) |

The embodiments of the invention in which an exclusive property or privilege is claimed are defined as follows:

1. A process for the preparation of a polyprenyl ketone derivative having the general formula:

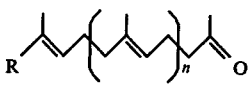

in which n is an integer of 1–5, and R represents a hydroxymethyl, formyl or carboxyl group, which comprises:
cultivating a microorganism belonging to the genus Nocardia identified as BPM 1613, FERM-P No. 1609, which shows an oxidizing activity on a compound having the general formula:

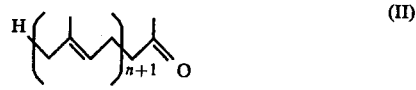

in which n is an integer of 1–5,
in a culture medium containing a compound of the general formula (II); and
recovering the oxidized product from the cultured medium.

2. A process as claimed in claim 1 in which the culture medium has a pH of from 6 to 8 and the cultivating step is performed under aerobic conditions, at 20° to 40° C., for from 2 to 5 days.

* * * * *